US006228346B1

(12) United States Patent
Zhang et al.

(10) Patent No.: US 6,228,346 B1
(45) Date of Patent: May 8, 2001

(54) PROPELLANT MIXTURES AND AEROSOLS FOR MICRONIZING MEDICAMENTS WITH COMPRESSED GAS

(75) Inventors: Zhengfeng Zhang, Tutzing; Martin Knoch, Berg, both of (DE)

(73) Assignee: Pari GmbH Spezialisten fur Effektive Inhalation, Starnberg (DE)

(*) Notice: Subject to any disclaimer, the term of this patent is extended or adjusted under 35 U.S.C. 154(b) by 0 days.

(21) Appl. No.: 09/171,695
(22) PCT Filed: Apr. 25, 1997
(86) PCT No.: PCT/EP97/02149
§ 371 Date: Dec. 9, 1998

§ 102(e) Date: Dec. 9, 1998

(87) PCT Pub. No.: WO97/40824

PCT Pub. Date: Nov. 6, 1997

(30) Foreign Application Priority Data

Apr. 25, 1996 (DE) ............................................ 196 16 573

(51) Int. Cl.[7] ................................ A61L 9/04; A61K 9/14

(52) U.S. Cl. ................................................ 424/45; 424/46

(58) Field of Search .......................................... 424/45, 46

(56) References Cited

U.S. PATENT DOCUMENTS

| | | | |
|---|---|---|---|
| 5,118,494 | 6/1992 | Schultz et al. . | |
| 5,126,123 | 6/1992 | Johnson . | |
| 5,182,097 | 1/1993 | Byron et al. . | |
| 5,185,094 | 2/1993 | Shiflett . | |
| 5,190,029 | 3/1993 | Byron et al. . | |
| 5,202,110 | 4/1993 | Dalby et al. . | |
| 5,225,183 * | 7/1993 | Purewal et al. | 424/45 |
| 5,301,664 | 4/1994 | Sievers et al. . | |
| 5,736,124 * | 4/1998 | Akehurst et al. | 424/45 |

FOREIGN PATENT DOCUMENTS

| | | |
|---|---|---|
| 4038203 | 11/1992 | (DE) . |
| 4123663 | 1/1993 | (DE) . |
| 372 777 | 11/1989 | (EP) . |
| 502 | 5/1992 | (EP) . |
| 518 600 | 6/1992 | (EP) . |
| 518 601 | 6/1992 | (EP) . |
| 526 002 | 7/1992 | (EP) . |
| 91/04011 | 4/1991 | (WO) . |
| 92/00062 | 1/1992 | (WO) . |
| 92/06675 | 4/1992 | (WO) . |
| 92/11190 | 7/1992 | (WO) . |
| 93/04671 | 3/1993 | (WO) . |

OTHER PUBLICATIONS

Michael E. Whitham, et al.; “Alternative Propellants: Proprietary Rights, Toxicological Issue and Projected Licensing Problems”, *Respiratory Drug Delivery IV;* 1994; pp. 203–209.

Pamela S. Zurer, “Looming Ban on Production of CFCs, Halons Spurs Switch to Substitutes”, *C&EN;* Nov. 15, 1993; pp. 12–18.

(List continued on next page.)

*Primary Examiner*—Thurman K. Page
*Assistant Examiner*—S. Tran
(74) *Attorney, Agent, or Firm*—Merchant & Gould P.C.

(57) ABSTRACT

Propellant mixtures and medicament aerosols which contain them are described for micronizing medicaments for pulmonary use. The propellant mixture is in a subcritical state and contains at least one component from a first class of propellant gasses and at least one component from a second class of propellant gasses. The first class includes propellant gasses with an evaporation enthalpy of 200 kJ/kg or less at 25° C. and a vapor pressure of 20 bars or more at 25° C., and the second class includes propellant gasses with an evaporation enthalpy of 300 kJ/kg or more at 25° C. and a vapor pressure of 10 bars or less at 25° C. By using this propellant mixture in a medicament aerosol, micronized medicaments are obtained in which approximately 80% by weight of the generated particles have less than 8 $\mu$m diameter.

31 Claims, 1 Drawing Sheet

OTHER PUBLICATIONS

Peter R. Byron, et al.; "Some Aspects of Alternative Propellant Solvency"; *Respiratory Drug Delivery IV;* 1994; pp. 231–242.

Ashley Woodcock; "Continuing Patient Care with Metered–Dose Inhalers"; *Journal of Aerosol Medicine;* 1995; vol. 8, pp. S–5 to S–10.

* cited by examiner

Fig. 1
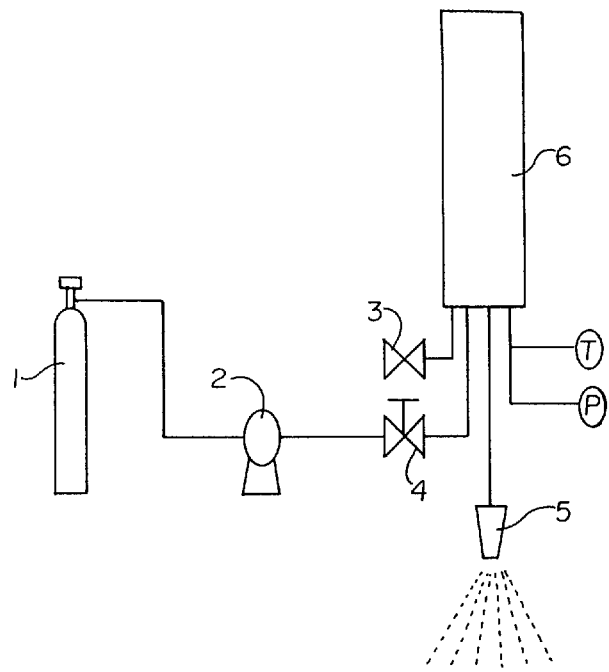
Fig. 2A
Fig. 2B
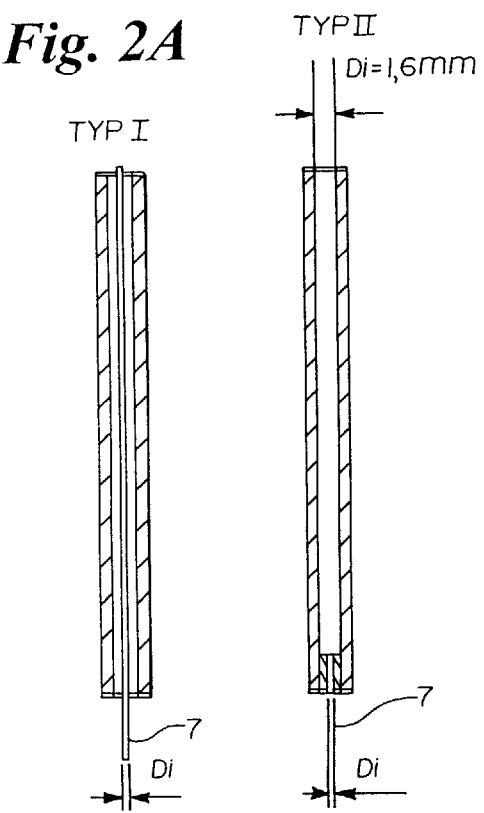

PROPELLANT MIXTURES AND AEROSOLS FOR MICRONIZING MEDICAMENTS WITH COMPRESSED GAS

BACKGROUND OF THE INVENTION

Field of the Invention

The invention relates to propellant mixtures and their use in pharmaceutical aerosols for pulmonary application.

Due to their technical benefits, fluorochlorohydrocarbons (CFCs) are currently still used as coolants in refrigeration and air-conditioning plants and as propellant gases in metered dose aerosols. Their environmentally harmful effects, particularly in terms of destruction of the ozone layer in the earth's atmosphere, have also prompted extensive research into harmless substitutes. In this way, there is also a need, in the field of aerosol production, to develop innovative and environmentally compatible propellants and manufacturing processes for aerosols.

A process of CFC-free aerosol preparation for use in special inhalers, "MDIs" (metered dose inhalers) is disclosed in U.S. Pat. No. 5,190,029. 1,1,1,2-tetrafluoroethane, also known as R 134a, is used as a propellant either on its own or mixed with various other hydrocarbons. The active pharmaceutical ingredient is salbutamol; oleic acid is added as a surface-active additive. The density, vapor pressures and other relevant properties of the formulations were measured, according to which just 22% to 39% of the generated aerosol particles have an aerodynamic diameter of less than or equal to 11.2 $\mu$m. WO 9304671 describes an aerosol composed of a medicinal agent, a glycerophosphatide and a propellant gas or propellant gas mixture of n-butane, dimethyl ether and propane. The presence of glycerophosphatides increases the medicinal agent's solubility in the propellant gas. By suitably adjusting the proportions of the various components, the system forms a homogeneous solution, i.e. not a suspension. This application document does not indicate whether sufficiently fine particles can be produced from this homogeneous solution.

Several patent applications and patent specifications propose using 1,1,1,2-tetrafluoroethane (R 134a, $CH_2FCF_3$) and 1,1,1,2,3,3,3-heptafluoropropane (R 227, $CF_3CHFCF_3$) as alternative propellants. Such documents include e.g. DE 4123663, DE 4038203, EP 526002, EP 512502, EP 518601, EP 518600, EP-A-372777, U.S. Pat. Nos. 5,182,097, 5,185,094, 5,118,494, 5,126,123, 5,190,029, 5,202,110, WO 9104011, WO 9200062, WO 9211190 and WO 9206675. Although these compounds do not contain chlorine and consequently do not have any harmful effects on the ozone layer of the earth's atmosphere, they exhibit a considerable greenhouse potential (Michael E. Whitham et al.: Respiratory Drug Delivery IV, 1994, 203; Pamela S. Zurer: Chem. En. News, 15 (11), 1993, 12).

The commercially available CFC metered dose aerosols exist in the form of a suspension of the active ingredient in the propellant. One or more surfactants are used to suspend a pharmaceutical in the propellant gas mixture which normally comprises dichlorodifluoromethane (R12), trichlorofluoromethane (R11) and 1,2-dichlorotetrafluoroethane (R114). The most commonly used surfactants are e.g. sorbitan trioleate, oleic acid and lecithin. These substances do however suffer from the drawback that they are insoluble in R134a and R227 (Peter R. Byron, et al.: Respiratory Drug Delivery IV, 1994, 237; Ashley Woodcock: Journal of Aerosol Medicine, 8 (Suppl. 2) 1995, p. 5).

In chemical engineering, compressed gases have already been in use for some time in order to extract and refine natural products. The properties of the components and phases involved in these processes under near critical conditions were only recently investigated more closely. The knowledge gained opened up possible ways of using dense gases in other processes too. This also includes the use in medical technology for the pulmonary application of drugs.

U.S. Pat. No. 5,301,664 describes a technique that can be used to produce various active ingredients as a fine mist by means of compressed carbon dioxide. These substances are first dissolved in the supercritical carbon dioxide, which is present as a single phase, under a pressure of 200 bar at a temperature close to the body temperature similar to an extraction process. Sudden expansion upon emerging from a nozzle into the surroundings causes fine pharmaceutical particles to be formed by condensation as a result of the solvent's reduced dissolving capacity. Use of a supercritical propellant medium does, however, also entail considerable disadvantages, particularly high outlay in terms of apparatus. The low solvency of carbon dioxide and the very high pressures needed in spite of potentially using an entrainer cause such an atomizer to have large dimensions. The pressure has to be maintained so as to prevent condensation in the pressure chamber, which would inevitably arise during discharge. This occurs by means of a mobile pressure chamber base, whose side facing away from the pressure chamber communicates with another compressed gas. This compressed gas has a sufficiently high vapor pressure. Nitrogen is e.g. used. In accordance with safety requirements, the compressed gas must be stored in gas cylinders which have to be carried along. A hand-held device is therefore out of the question. The withdrawal of active ingredient is regulated by a manually operated valve. The withdrawn drug dosage is therefore determined by the duration of opening. It is also complicated, in technical terms, to charge the components, i.e. fill up the atomizer.

The pharmaceutical aerosol formulations in the prior art consequently need to be improved, especially with regard to the propellant. The present invention's object is therefore to provide improved and environmentally friendly propellants and aerosol formulations which contain them. According to the invention, the micronization of drugs for pulmonary administration is to be particularly realized by means of dense gases, though avoiding halogenated hydrocarbons. The pharmaceutical particles generated in this way are to be easily respirable, i.e. exhibit as small a particle size as possible. Handling and outlay in terms of apparatus are also to be relatively simple, for which purpose the drugs are to be micronized in moderate conditions, i.e. at a low pressure and temperature (room temperature) and with conventional nozzle shapes.

It is known that some pharmaceuticals are soluble in liquid dimethyl ether, propane, butane and other hydrocarbons. The vapor pressures of these propellant gases at room temperature are in the range of up to approx. 10 bar. This property makes them suitable for an aerosol formulation, but a crucial problem lies in their very considerable evaporation enthalpy. When such a formulation is sprayed, the propellant gas does not evaporate sufficiently quickly. The drug therefore cannot be micronized very finely, which impedes the pharmaceutical's respirability.

The evaporation enthalpy of several other gases, such as carbon dioxide, sulfur hexafluoride and ethane, is much smaller. But they generally have a very poor dissolving capacity and a relatively high vapor pressure. As already mentioned above, a pressure of 200 bar or more is e.g. necessary when an appreciable amount of the drug is dissolved in supercritical carbon dioxide. For this reason, carbon dioxide and sulfur hexafluoride are equally unsuitable as propellant gases for a reasonable and economically beneficial aerosol formulation.

SUMMARY OF THE INVENTION

It has now surprisingly been found that propellant gases with a low evaporation enthalpy, such as carbon dioxide, sulfur hexafluoride and ethane, can be used in the subcritical state in a pharmaceutical aerosol, without entailing the aforementioned disadvantages, if they are mixed with another gas that has a high evaporation enthalpy and a low vapor pressure, such as butane, propane or dimethyl ether. All these components can be completely mixed together in a liquid state. The favorable properties of both components are unexpectedly preserved, whereas the unfavorable ones are compensated for. The added gas has two functions: to decrease the overall system's vapor pressure and to increase the system's dissolving capacity. The system's evaporation enthalpy is still sufficiently small, with the result that problems do not arise during evaporation. Due to the presence of non-inflammable gas, the system's inflammability is also substantially reduced.

In accordance with the invention, the above object is solved by a special propellant mixture for pharmaceutical aerosols so as to micronize the drugs for pulmonary application. This propellant mixture is present in the subcritical state and contains at least one component from a first class of propellant gases and at least one component from a second class of propellant gases, with the first class comprising propellant gases having an evaporation enthalpy at 25° C. of 200 kJ/kg or less and a vapor pressure at 25° C. of more than 20 bar, and the second class comprising propellant gases having an evaporation enthalpy at 250C of 300 kJ/kg or more and a vapor pressure at 25° C. of 10 bar or less.

BRIEF DESCRIPTION OF THE DRAWING

FIG. 1 is an illustration of the system used in accordant with the invention comprises a gas cylinder, a high-pressure pump, a safety valve, a check valve, a spray nozzle, and an autoclave.

FIG. 2*a* and 2*b* depict various nozzles used to produce aerosols in accordant with the invention comprises a nozzle aperture.

DETAILED DESCRIPTION OF THE INVENTION

Key characteristics of representatives of the two propellant gas classes used according to the invention are as follows.

Propellant gas class 1:

At room temperature (25° C.), these gases exhibit a high vapor pressure of 20 bar or more, preferably 20 to 70 bar, and a small evaporation enthalpy of 200 kJ/kg or less, preferably 180 to 50 kJ/kg. Such gases include sulfur hexafluoride, carbon dioxide and ethane. Their poor dissolving capacity as regards the majority of organic substances, particularly pharmaceuticals, is typical.

Propellant gas class 2:

These gases have, on the other hand, a relatively low vapor pressure at room temperature (25° C.) of 10 bar or less, preferably 2 to 10 bar, and a high evaporation enthalpy at 25° C. of 300 kJ/kg or more, preferably 340 to 450 kJ/kg. Preferred agents are dimethyl ether, propane, butane and pentane. These gases frequently exhibit a good dissolving capacity for a great many organic substances.

The invention also relates to a pharmaceutical aerosol for pulmonary application; in addition to one or more pharmaceutical substances, this aerosol contains the aforementioned propellant mixture.

The propellant mixtures according to the invention preferably contain one or more propellant gases from the 1st propellant gas class having a percentage content, relative to the propellant mixture, of 10 to 80 wt. %, with particular preference for 15 to 60 wt. %, and one or more propellant gases from the 2nd propellant gas class having a percentage content ranging from 20 to 90 wt. %, with particular preference for 40 to 85 wt. %. The propellant mixture may also contain other propellant gases, though it preferably comprises just those from Classes 1 and 2. The pharmaceutical may be present in the aerosol composition in a dissolved state (solution aerosol) or in a suspended state (suspension aerosol).

As far as a suspension aerosol is concerned, what is also of consequence is the original particle size of the pharmaceutical to be suspended in the propellant mixture. Since the particle size is indeed (undesirably) increased during the spraying process, but virtually cannot be reduced in size, the pharmaceutical should already be present in a sufficiently fine form before being introduced into the propellant, i.e. reduced to a particle diameter of less than 8 $\mu$m. The fine particles can also be more easily suspended.

On account of their physical properties, such as vapor pressure and evaporation enthalpy, the propellant combinations of sulfur hexafluoride and butane, sulfur hexafluoride and dimethyl ether, ethane and butane, and ethane and dimethyl ether are particularly suitable for a suspension aerosol. Due to the excellent dissolving capacity of dimethyl ether, the propellant combinations of sulfur hexafluoride and dimethyl ether, and ethane and dimethyl ether are particularly suitable for a solution aerosol.

Many drugs are easily soluble in lower alcohols such as ethanol, propanol or isopropanol, as well as water, acetone and several other solvents. To improve the solubility of pharmaceuticals in a propellant gas mixture used according to the invention in a solution aerosol, compounds such as solubilizers or entrainers can be added thereto.

Surfactants are frequently added in a suspension aerosol for enhanced suspension of the pharmaceutical. A suspension aerosol formulation requires the surfactant used to be soluble in the propellant mixture. The conventional surfactants, such as oleic acid, lecithin and sorbitan trioleate, are easily soluble in the 2nd propellant gas class and are also soluble in the propellant gas mixture used here. In consequence, such surfactants can be used without difficulty in the production of a suspension aerosol formulation.

The propellant mixture according to the invention is used in the subcritical state in a pharmaceutical aerosol for pulmonary application so as to micronize the pharmaceutical, with about 80 wt. %, preferably about 90 wt. % and particularly preferably about 100 wt. % of the micronized pharmaceutical particles, i.e. those generated by spraying, having a diameter of less than 8 $\mu$m. In another preferred embodiment, about 80 wt. %, preferably about 90 wt. % and particularly preferably about 100 wt. % of the micronized pharmaceutical particles have a diameter of less than 5 $\mu$m. The percentages each relate to the total mass of the produced pharmaceutical particles "dried" after evaporating the propellant. These particles therefore have a smaller mass and are not so easily precipitated in the mouthpiece of the metered dose aerosol or in the spacer. Improved respirability means that not only the bronchial or upper pulmonary region, but also more deeply lying sections of the lungs and pulmonary alveoli are reached. This is not only a decisive advantage when the lung itself represents the affected organ to be treated, the resorption of systemic-action pharmaceuticals is also improved.

According to the invention, the propellant mixture is used in a pharmaceutical composition, viz. a pharmaceutical aerosol, for pulmonary application. The amount of propellant mixture in the finished pharmaceutical aerosol is preferably 80 to 99.99 wt. %, with particular preference for 90 to 99.99 wt. %. In addition to the pharmaceutical, this composition contains the above-described propellant mixture and optionally other common, pharmaceutically compatible diluents, excipients, entrainers, solubilizers and surfactants. The pharmaceutical may be present in the aerosol composition as a solution or suspension with a percentage content of 0.01 to 5 wt. %, preferably 0.03 to 1 wt. %. The operating pressure of the composition is 2 to 100, preferably 3 to 50 bar, with particular preference for 5 to 20 bar. For micronization, a spray nozzle common for this purpose is used.

In a preferred embodiment of the newly developed pharmaceutical aerosol, the propellant mixture solely comprises one or more components from the above two classes. The aforementioned solubilizers and/or surfactants can also be optionally present.

To achieve specific or improved effects, a combination of different active ingredients with varying percentage contents can be used in an aerosol formulation, e.g. combinations of ipratropium bromide and fenoterol, salbutamol and disodium cromoglicinic acid, and salbutamol and beclometason-17,21-dipropionate.

In all those instances in which a surfactant is used, the weight ratio of pharmaceutical to surfactant ranges from 100:1 to 1:100, preferably from 20:1 to 1:10.

According to the invention, the pharmaceutical aerosol formulations, each relative to the total formulation, preferably have the following compositions unless otherwise indicated:

Propellant gas class 1: 10 to 80 wt. %, particularly preferred 15 to 60 wt. %

Propellant gas class 2: 20 to 90 wt. %, particularly preferred 40 to 85 wt. %

(each relative to the propellant mixture)

Propellant mixture: 80 to 99.99 wt. %, particularly preferred 90 to 99.99 wt. %

Pharmaceuticals: 0.01 to 5 wt. %, particularly preferred 0.03 to 1 wt. %

Surfactants: up to S wt. %, particularly preferred up to 1 wt. %

Solubilizers (entrainers): up to 10 wt. %, particularly preferred up to 2 wt. %.

(each relative to finished pharmaceutical aerosols)

WORKING EXAMPLES

The following experimental values help to explain the invention in more detail.

DESCRIPTION OF THE DRAWINGS

The system (FIG. 1) comprises a gas cylinder 1, a high-pressure pump 2, a safety valve 3, a check valve 4, a spray nozzle 5, and an autoclave 6. T is a thermometer and P is a manometer. The autoclave has a 200 ml capacity. In some tests, a small autoclave with a 32 ml capacity is also used. This entails a smaller amount of pharmaceuticals and other substances.

The autoclave is mounted in a swing frame secured to a trestle by means of bearing brackets. The frame is oscillated upwards and downwards by about 30° via a motor with an eccentric rod and conrod. After the autoclave is cleaned, it is charged with a drug and optionally additives as well, and sealed with a lid. The high-pressure pump is used to pump dimethyl ether, propane or butane out of the cylinder, which is positioned on a balance, into the autoclave. The feed quantity can be read off from the balance. Since the vapor pressure of $CO_2$, $SF_6$ or ethane is greater than the test pressure, these substances can simply be fed into the autoclave from a cylinder.

After the pressure in the autoclave has reached the desired value, it is agitated for about 90 minutes. It is then not moved for 30 minutes, causing all the undissolved substances to separate from the gas mixture. A high-pressure viewing cell with a 35 ml volume is used to evaluate the stability of a suspension. The viewing cell has a large viewing diameter of 30 mm, making it much easier to observe the suspension.

FIG. 2 shows various conventional nozzles that were used to produce aerosols. These nozzles differ in terms of shape and size of the nozzle aperture 7 (Di is the particular internal diameter). Type I includes those nozzles with a nozzle aperture of 0.35 mm, 0.50 mm, 1.00 mm and 1.60 mm; Type II includes those nozzles with a nozzle aperture of 0.20 mm, 0.30 mm and 0.50 mm. The autoclave is connected by a valve to a nozzle. The expansion of the liquefied gas mixture occurs via a starting pressure in the range of 10 to 40 bar up to the ambient pressure. This enables small particles to be produced. A slide is located beneath the nozzle at a distance of about 40–100 mm, perpendicular to the direction of spray. A microscope (magnification factor 1000) is used to observe and evaluate qualitatively the particles on the slide.

The solubility of a pharmaceutical is determined by taking samples. After expansion, the solid dissolved in the gas mixture is deposited into a test tube, the amount of gas is determined using a volumetric gas meter. The deposited amount of solid is gravimetrically determined, the ratio of the two gases is analyzed by gas chromatography.

Results and discussion

Based on this method, various drugs are successfully atomized. The diameters of all the micronized pharmaceutical particles are less than 8 $\mu$m, in some tests they are less than 5 $\mu$m or 2 $\mu$m respectively. The specific test conditions and their results are depicted in the following section on "Examples".

As regards the aerosol formulation having a pharmaceutical dissolved therein, the amount of active ingredient fed into the autoclave is in most cases larger than the amount needed for a saturated solution. This leads to an additional solid phase which can in such instances be seen by means of the viewing cell.

Since the concentration of pharmaceuticals in gas mixtures is normally much smaller than 1 wt. % relative to the overall composition, the pharmaceutical has practically no influence on the binary system phase behavior. Due to the fact that the phase equilibria are known in some systems, such as $SF_6$/propane, dimethyl ether/$CO_2$, the ratio of both components can be determined in accordance with pressure and temperature. For control purposes, some gas samples are also analyzed by means of gas chromatography.

The solubilities of the drugs examined in this study in liquid dimethyl ether usually amount to more than 0.1 wt. %, only terbutaline sulfate and ipratropium bromide are somewhat less readily soluble. The solubilities in liquid n-butane are generally smaller than in liquid dimethyl ether. In this way, the saturated concentrations of budesonide and beclometason-17,21-dipropionate in n-butane are about 0.06 wt. % and 0.03 wt. % respectively.

Solubility is reduced by adding a gas from the 1st propellant gas class, but for a great many drugs, the concentrations are still so large that they are sufficient for inhalation therapy. For instance, the solubility of salbutamol in liquid dimethyl ether is approx. 0.23 wt. %. Solubility decreases by adding carbon dioxide: if the ratio of $CO_2$/dimethyl ether is 39:61, the salbutamol content in a saturated state of the liquid mixture is approx. 0.18 wt. %. The salbutamol content of the liquid mixture is 0.06 wt. % for a ratio of 64:36.

Phospholipids can act as a surfactant in an aerosol formulation. They can be completely mixed with liquid dimethyl ether, are easily soluble in liquid propane and butane, but are insoluble in $CO_2$, $SF_6$ and ethane.

In all the studies on phase equilibrium measurement and in the spray tests, two fluid phases, one gas phase and one liquid phase, are produced in the autoclave; these phases are in an equilibrium state. The content of the liquid phase is decreased both during sampling and during spraying. As long as the liquid phase is still present, the pressure does not alter considerably. Under the examined conditions, the gas-phase density is very small with respect to the liquid-phase density. For this reason, the composition of the liquid phase and its dissolving capacity do not vary appreciably during aerosol generation. Since the concentration of a drug in the liquid phase is stable during the spraying process, it is possible to obtain an aerosol formulation with a precise dosage. This is a crucial and beneficial property of the system as far as practical application is concerned.

As in the case of commercially available CFC-based metered dose aerosols, various entrainers or surfactants such as ethanol, water, acetone, oleic acid and lipids can also be used in this process in order to increase the solubility of a pharmaceutical in the gas mixture or to stabilize the suspension.

Table 1 depicts the physical characteristics of some of the most important propellant gases. The parameters which are essential to the invention are vapor pressure and evaporation enthalpy. By way of comparison, R 11, R 12 and R 114 are also included as the three propellant gases currently most frequently used in metered dose aerosols.

According to the invention, no supercritical gas mixture is used. Because of the gas mixture's relatively low vapor pressure, the aerosol container can therefore be lent correspondingly small dimensions. This simplifies handling.

The solubility of a pharmaceutical in a propellant gas mixture also depends on temperature. The temperature of a metered dose aerosol is upwardly restricted because the drug may be destroyed by too high a temperature. Room temperature is therefore preferred as regards practical application.

These analyses show that when two gases from both the classes are combined, much lower pressures are needed than when a supercritical component is used. This combination also has a positive effect on the gas mixture's solubility. The gas mixture's vapor pressure, evaporation enthalpy and dissolving capacity can be adjusted in a large range in that the ratio of the low vapor pressure component to the high vapor pressure component is varied.

The operating pressure of a system depends on its composition (pharmaceutical, gas mixture and other entrainers or surfactants), but ranges from 2 to 100 bar, preferably 3 to 50 bar. As concerns the dimethyl ether/$CO_2$ system, the vapor pressure ranges from 5 to 65 bar, preferably from 30 to 40 bar. Higher pressure and lower evaporation enthalpy promote the formation of fine particles during the spray process. The $CO_2$ content has to be increased for a higher pressure, which causes the mixture to exhibit a poor dissolving capacity. The optimum conditions can be easily ascertained by preliminary tests. A lower pressure is preferred for practical handling, for which purpose suitable gases can be used. By using ethane instead of $CO_2$, the operating pressure can be reduced by about 20 bar; if sulfur hexafluoride is used, the pressure drops further (Table 1).

The suitable nozzle aperture of a spray nozzle depends on the operating pressure. A nozzle aperture of approx. 0.3 to approx. 0.5 mm, as is usually the case in the pressure range used for pulmonary application, has proved to be beneficial.

TABLE 1

Physical properties of some propellant gases

| Gas | | Molar | Critical temperature | Critical pressure | Vapor pressure at 25° C. | Evaporation enthalpy, at 25° C. |
|---|---|---|---|---|---|---|
| Name | Formula | weight | ° C. | bar | bar | kJ/kg |
| Trichloro-fluoromethane (R11) | $CCl_3F$ | 137.5 | 198 | 44.0 | 1 | 181 |
| Dichloro-difluoromethane (R12) | $CCl_2F_2$ | 121 | 112 | 41.2 | 6.5 | 140 |
| 1,2-dichloro-tetrafluoro-ethane (R114) | $C_2Cl_2F_4$ | 171 | 145.7 | 32.6 | 2,1 | 130 |
| Tetrafluoro-ethane (R134a) | $C_2H_2F_4$ | 102 | 101 | 40.6 | 6.7 | 178.4 |
| Ethane | $CH_3CH_3$ | 30 | 32.3 | 48.8 | 41 | 167 |
| Sulfur hexafluoride | $SF_6$ | 146 | 45.5 | 37.6 | 24 | 64.9 |
| Carbon dioxide | $CO_2$ | 44 | 31.1 | 73.8 | 65 | 123 |
| DME | $CH_3OCH_3$ | 46 | 127 | 52.7 | 6.3 | 396 |
| n-butane | $C_4H_{10}$ | 58 | 152 | 38 | 2.4 | 364 |
| Propane | $CH_3CH_2CH_3$ | 44.1 | 96.7 | 42.5 | 9.6 | 343 |

Example 1

40 mg budesonide (Budes) and 4 mg lecithin (Leci) are fed into a pressure vessel. The pressure vessel has a capacity of 32 ml and is provided with a manometer and a 0.50 mm diameter spray nozzle. The air is removed from the vessel by evacuation. About 14 g n-butane and 6 g $SF_6$ (Sulf) are then pumped in. The vapor pressure of the mixture is 10 bar at 25° C. Agitation causes lecithin to be dissolved in this liquid mixture and budesonide to be suspended therein. The suspension formed is very stable. Only after several minutes is the precipitation of budesonide clearly observed. The precipitated budesonide can easily be re-suspended by agitation. The suspension is sprayed onto a clean and dry slide via an expansion valve by means of the spray nozzle at a distance of about 5 cm from the nozzle mouth, perpendicular to the direction of spray. A microscope (magnification factor 1000) is used to observe the particles on the slide. The vast majority of the particles has a diameter of less than 2 $\mu$m. There are very few particles with a diameter between 2 and 4 $\mu$m. Particles that are even larger are not found.

Example 2

24 mg salbutamol (Salb) and 4 mg lecithin are fed into a pressure vessel. The pressure vessel has a capacity of 32 ml and is provided with a manometer and a 0.50 mm diameter spray nozzle. The air in the vessel is removed by evacuation. About 8.4 g n-butane and 3.6 g ethane are then pumped in. The vapor pressure of the mixture is 15 bar at 25° C. Agitation causes lecithin to be dissolved in this liquid mixture and salbutamol to be suspended therein. The suspension formed is very stable. Only after several minutes is the precipitation of salbutamol clearly observed. The precipitated salbutamol can easily be re-suspended by agitation. The suspension is sprayed onto a clean and dry slide via an expansion valve by means of the spray nozzle at a distance of approx. 6 cm from the nozzle mouth, perpendicular to the direction of spray. A microscope (magnification factor 1000) is used to observe the particles on the slide. The vast majority of the particles has a diameter of less than 2 $\mu$m. There are very few particles with a diameter between 2 and 5 $\mu$m. Particles larger than 5 $\mu$m are not found.

Example 3

180 mg beclometason-17,21-dipropionate (BDP) are fed into an autoclave, as shown in FIG. 1. The autoclave has a capacity of 200 ml and is provided with a manometer and a 0.30 mm diameter spray nozzle. After evacuation, approx. 78 g dimethyl ether (DME) and 78 g $SF_6$ are pumped in. The vapor pressure of the mixture is 20 bar at 25° C. Agitation causes beclometason-17,21-dipropionate to be dissolved in this liquid mixture. The homogeneous solution formed is sprayed onto a clean and dry slide via an expansion valve by means of the spray nozzle at a distance of approx. 6 cm from the nozzle mouth, perpendicular to the direction of spray. A microscope (magnification factor 1000) is used to observe the particles on the slide. The vast majority of the particles has a diameter of less than 5 $\mu$m. There are very few particles with a diameter of over 5 $\mu$m.

Example 4

50 mg terbutaline sulfate (Terbu) and 5 mg lecithin are fed into a pressure vessel. The pressure vessel has a capacity of 32 ml and is provided with a manometer and a 0.50 mm diameter spray nozzle. The air in the vessel is removed by evacuation.

Approx. 8 g n-butane and 3 g ethane are then pumped in. The vapor pressure of the mixture is 15 bar at 25° C. Agitation causes lecithin to be dissolved in this liquid mixture and terbutaline sulfate to be suspended therein. The suspension formed is stable. Only after several minutes is the precipitation of terbutaline sulfate clearly observed. The precipitated terbutaline sulfate can easily be re-suspended by agitation. The suspension is sprayed onto a clean and dry slide via an expansion valve by means of the spray nozzle at a distance of about 6 cm from the nozzle mouth, perpendicular to the direction of spray. A microscope (magnification factor 1000) is used to observe the particles on the slide. The vast majority of the particles has a diameter of less than 3 $\mu$m. There are very few particles with a diameter between 3 and 6 $\mu$m. Particles with a diameter of more than 6 $\mu$m are not found.

Example 5

0.1 g disodium cromoglicinic acid (DSCG) is fed into an autoclave, as shown in FIG. 1. The autoclave has a capacity of 200 ml and is provided with a manometer and a 0.35 mm diameter spray nozzle. After evacuation, approx. 20 g ethane and 70 g DME are pumped in. The vapor pressure of the mixture is 18 bar at 25° C. Agitation causes disodium cromoglicinic acid to be dissolved in this liquid mixture. The homogeneous solution formed is sprayed onto a clean and dry slide via an expansion valve by means of the spray nozzle at a distance of about 6 cm from the nozzle mouth, perpendicular to the direction of spray. A microscope (magnification factor 1000) is used to observe the particles on the slide. The vast majority of the particles has a diameter of less than 6 $\mu$m. There are very few particles with a diameter of more than 6 $\mu$m.

Example 6

10 mg ipratropium bromide (Iprat) and 2 mg lecithin are fed into a pressure vessel. The pressure vessel has a capacity of 32 ml and is provided with a manometer and a 0.50 mm diameter spray nozzle. The air is removed from the vessel by evacuation. Approx. 13 g n-butane and 5 g $SF_6$ are then pumped in. The vapor pressure of the mixture is 9 bar at 25° C. Agitation causes lecithin to be dissolved in this liquid mixture and ipratropium bromide to be suspended therein. The suspension formed is stable. Only after several minutes is the precipitation of ipratropium bromide clearly observed. The precipitated ipratropium bromide can easily be re-suspended by agitation. The suspension is sprayed onto a clean and dry slide via an expansion valve by means of the spray nozzle at a distance of about 5 cm from the nozzle mouth, perpendicular to the direction of spray. A microscope (magnification factor 1000) is used to observe the particles on the slide. The vast majority of the particles has a diameter of less than 4 $\mu$m. There are very few particles with a diameter of over 4 $\mu$m.

Example 7

25 mg salbutamol are fed into a pressure vessel. The pressure vessel has a capacity of 32 ml and is provided with a manometer and a 0.50 mm diameter spray nozzle. The air is removed from the vessel by evacuation. Approx. 12 g DME and 8 g $SF_6$ are then pumped in. The vapor pressure of the mixture is 17 bar at 25° C. Agitation causes salbutamol to be dissolved in this liquid mixture. The homogeneous solution formed is sprayed onto a clean and dry slide via an expansion valve by means of the spray nozzle at a distance of about 5 cm from the nozzle mouth, perpendicular to the direction of spray. A microscope (magnification factor 1000) is used to observe the particles on the slide. The vast majority of the particles has a diameter of less than 5 μm. There are very few particles with a diameter of more than 5 μm.

Example 8

60 mg amphotericin B (Amph) and 2 mg lecithin are fed into a pressure vessel. The pressure vessel has a capacity of 32 ml and is provided with a manometer and a 0.50 mm diameter spray nozzle. The air is removed from the vessel by evacuation. Approx. 8 g dimethyl ether and 12 g $SF_6$ are then pumped in. The vapor pressure of the mixture is 21 bar at 25° C. Agitation causes lecithin to be dissolved in this liquid mixture and amphotericin B to be suspended therein. The suspension formed is very stable. Only after several minutes is the precipitation of amphotericin B clearly observed. The precipitated amphotericin B can easily be re-suspended by agitation. The suspension is sprayed onto a clean and dry slide via an expansion valve by means of the spray nozzle at a distance of about 5 cm from the nozzle mouth, perpendicular to the direction of spray. A microscope (magnification factor 1000) is used to observe the particles on the slide. The vast majority of the particles has a diameter of less than 2 μm. There are very few particles with a diameter between 2 and 6 μm. Particles with a diameter of over 6 μm are not found.

Example 9

15 mg salbutamol, 10 mg beclometason-17,21-dipropionate and 4 mg lecithin are fed into a pressure vessel. The pressure vessel has a capacity of 32 ml and is provided with a manometer and a 0.50 mm diameter spray nozzle. The air is removed from the vessel by evacuation. Approx. 8.5 g n-butane and 3.8 g ethane are then pumped in. The vapor pressure of the mixture is 15 bar at 25° C. Agitation causes lecithin to be dissolved in this liquid mixture and salbutamol and beclometason-17,21-dipropionate to be suspended therein. The suspension formed is very stable. Only after several minutes is the precipitation of the pharmaceuticals clearly observed. The precipitated drugs can easily be re-suspended by agitation. The suspension is sprayed onto a clean and dry slide via an expansion valve by means of the spray nozzle at a distance of about 6 cm from the nozzle mouth, perpendicular to the direction of spray. A microscope (magnification factor 1000) is used to observe the particles on the slide. The vast majority of the particles has a diameter of less than 3 μm. There are very few particles with a diameter between 3 and 5 μm. Particles with a diameter of over 5 μm are not found.

Comparative Example 1

40 mg budesonide are fed into a pressure vessel. The pressure vessel has a capacity of 32 ml and is provided with a manometer and a 0.50 mm diameter spray nozzle. The air is removed from the vessel by evacuation. Approx. 16 g dimethyl ether are then pumped in. The vapor pressure of the system is 6 bar at 25° C. Agitation causes budesonide to be dissolved in liquid dimethyl ether. The homogeneous solution is sprayed onto a clean and dry slide via an expansion valve by means of the spray nozzle at a distance of about 5 cm from the nozzle mouth, perpendicular to the direction of spray. A microscope (magnification factor 1000) is used to observe the particles on the slide. The diameters of the resultant budesonide particles vary considerably: some particles have a diameter of less than 10 μm, most particles have a diameter in the range of 10 to 30 μm, some particles are over 30 μm.

Comparative Example 2

60 mg amphotericin B and 4 mg lecithin are fed into a pressure vessel. The pressure vessel has a capacity of 32 ml and is provided with a manometer and a 0.50 mm diameter spray nozzle. The air is removed from the vessel by evacuation. Approx. 17 g dimethyl ether are then pumped in. The vapor pressure of the system is 6 bar at 25° C. Agitation causes lecithin to be dissolved in this liquid mixture, and amphotericin B to be suspended therein. The suspension formed is very stable. Only after several minutes is the precipitation of amphotericin B clearly observed. The precipitated amphotericin B can easily be resuspended by agitation. The suspension is sprayed onto a clean and dry slide via an expansion valve by means of the spray nozzle at a distance of about 5 cm from the nozzle mouth, perpendicular to the direction of spray. A microscope (magnification factor 1000) is used to observe the particles on the slide. The diameters of the resultant particles vary considerably: some particles have a diameter of less than 6 μm, most particles have a diameter in the range of 6 to 20 μm, some particles have a diameter of more than 20 μm, in some cases of even more than 50 μm.

Comparative Example 3

40 mg salbutamol and 8 mg lecithin are fed into a pressure vessel. The pressure vessel has a capacity of 32 ml and is provided with a manometer and a 0.50 mm diameter spray nozzle. The air in the vessel is removed by evacuation. Approx. 30 g sulfur hexafluoride are then pumped in. The vapor pressure of the system is 24 bar at 25° C. Agitation causes neither lecithin nor salbutamol to be dissolved or suspended in liquid sulfur hexafluoride. They rapidly float to the surface due to their lighter specific weight in comparison to that of sulfur hexafluoride. The mixture is sprayed onto a clean and dry slide via an expansion valve by means of the spray nozzle at a distance of about 6 cm from the nozzle mouth, perpendicular to the direction of spray. If the time between agitating the formulation and spraying is more than 10 seconds, practically no salbutamol or lecithin are sprayed. If spraying immediately takes place after agitation, very few fine particles with a diameter in the range of about 1 to 3 μm are found on the slide.

The results of Examples 1 to 9 and Comparative Examples 1 to 3 are summarized in Table 2. It is shown that only when propellant gases from both the aforementioned classes are combined are the desired fine particle sizes obtained. If just one propellant gas from one class is used, no particles are obtained whatsoever or particles are obtained to an inadequate extent, or the particle size is unacceptably high.

TABLE 2

| Examples according to the invention | Pharmaceutical | | Surfactant | | | Propellant gas 1 | | | Propellant gas 2 | | | P (25° C.) bar | System ml | Particles μm |
|---|---|---|---|---|---|---|---|---|---|---|---|---|---|---|
| | Name | mg | Wt. % | Name | mg | Wt. % | Name | g | Wt. % | Name | g | Wt. % | | | |
| 1 | Budes | 40 | 0.2 | Leci | 4 | 0.02 | Sulf | 6 | 30 | Butan | 14 | 70 | 10 | 32 | 2~4 |
| 2 | Salb | 24 | 0.2 | Leci | 4 | 0.03 | Ethan | 3.6 | 30 | Butan | 8.4 | 70 | 15 | 32 | 2~5 |
| 3 | BDF | 180 | 0.12 | — | | | Sulf | 78 | 50 | DME | 78 | 50 | 20 | 200 | 5 |
| 4 | Terbu | 50 | 0.45 | Leci | 5 | 0.05 | Ethan | 3 | 27 | Butan | 8 | 72 | 15 | 32 | 3~6 |
| 5 | DSCG | 100 | 0.11 | — | | | " | 20 | 22 | DME | 70 | 77.7 | 18 | 200 | 6 |
| 6 | Iprat | 10 | 0.05 | Leci | 2 | 0.01 | Sulf | 5 | 27.7 | Butan | 13 | 72.2 | 9 | 32 | 4 |
| 7 | Salb | 25 | 0.125 | — | | | " | 8 | 40 | DME | 12 | 60 | 17 | 32 | 5 |
| 8 | Amph | 60 | 0.3 | Leci | 2 | 0.01 | " | 12 | 60 | " | 8 | 40 | 21 | 32 | 2~6 |
| 9 | Salb | 15 | 0.12 | Leci | 4 | 0.03 | Ethan | 3.8 | 31 | Butan | 8.5 | 69 | 15 | 32 | 2~5 |
| | BDP | 10 | 0.08 | | | | | | | | | | | | |
| Comparative examples | | | | | | | | | | | | | | | |
| 1 | Budes | 40 | 0.25 | — | — | — | — | — | — | DME | 16 | 99.8 | 6 | 32 | 10~30 |
| 2 | Amph | 60 | 0.35 | Leci | 4 | 0.02 | — | — | — | DME | 17 | 99.6 | 6 | 32 | 6~20 |
| 3 | Salb | 40 | 0.13 | Leci | 8 | 0.03 | Sulf | 30 | 99.8 | — | — | — | 24 | 32 | — |

What is claimed is:

1. A propellant mixture for pharmaceutical aerosols for micronizing the pharmaceuticals for pulmonary application, wherein
said propellant mixture exists in a subcritical state and includes at least one component from a first class of propellant gases and at least one component from a second class of propellant gases, said first class comprising propellant gases having an evaporation enthalpy at 25° C. of 200 kJ/kg or less and a vapor pressure at 25° C. of 20 bar or more, and said second class comprising propellant gases having an evaporation enthalpy at 25° C. of 300 kJ/kg or more and a vapor pressure at 25° C. of 10 bar or less, wherein at least about 80 wt. % of the micronized pharmaceuticals have a diameter of less than 8 μm.

2. A propellant mixture according to claim 1, wherein said first class comprises propellant gases having an evaporation enthalpy at 25° C. of 50 to 180 kJ/kg and a vapor pressure at 25° C. of 20 to 70 bar.

3. A propellant mixture according to claim 1, wherein said second class comprises propellant gases having an evaporation enthalpy at 25° C. of 340 to 450 kJ/kg and a vapor pressure at 25° C. of 2 to 10 bar.

4. A propellant mixture according to claim 1, wherein the percentage content of said first class of propellants is 10 to 80 wt. % relative to said propellant mixture.

5. A propellant mixture according to claim 1, wherein the percentage content of said second class of propellant gases is 20 to 90 wt. % relative to said propellant mixture.

6. A propellant mixture according to claim 1, wherein the propellant gases of said first class are chosen from carbon dioxide, sulfur hexafluoride and ethane.

7. A propellant mixture according to claim 1, wherein the propellant gases of said second class are chosen from dimethyl ether, propane, butane and pentane.

8. A propellant mixture according to claim 1, wherein said propellant mixture comprises one or more propellant gases of said first class and one or more propellant gases of said second class.

9. A propellant mixture according to claim 1, wherein said propellant mixture for a suspension aerosol comprises propellant combinations chosen from sulfur hexafluoride and butane, sulfur hexafluoride and dimethyl ether, ethane and butane, and ethane and dimethyl ether.

10. A propellant mixture according to claim 1, wherein said propellant mixture for a solution aerosol comprises propellant combinations chosen from sulfur hexafluoride and dimethyl ether, and from ethane and dimethyl ether.

11. A pharmaceutical aerosol for micronizing the pharmaceutical for pulmonary application, wherein said pharmaceutical aerosol contains a propellant mixture according to claim 1.

12. A pharmaceutical aerosol according to claim 11, wherein said pharmaceutical is present in said pharmaceutical aerosol in a dissolved or suspended state as a percentage content of 0.01 to 5 wt. % relative to said pharmaceutical aerosol.

13. A pharmaceutical aerosol according to claim 11, wherein said propellant mixture is present as a percentage content of 80 to 99.99 wt. % relative to said pharmaceutical aerosol.

14. A pharmaceutical aerosol according to claim 11, wherein said pharmaceutical is chosen from the active ingredients budesonide, salbutamol, beclometason-17,21-dipropionate, terbutaline sulfate, disodium cromoglicinic acid, ipratropium bromide, amphotericin B and combinations thereof.

15. A pharmaceutical aerosol according to claim 11, wherein said pharmaceutical aerosol also contains solubilizers for said pharmaceutical.

16. A pharmaceutical aerosol according to claim 15, wherein said solubilizers are chosen from alcohols, water and acetone.

17. A pharmaceutical aerosol according to claim 11, wherein said pharmaceutical aerosol also contains surfactants.

18. A pharmaceutical aerosol according to claim 17, wherein said surfactants are chosen from oleic acid, lecithin and sorbitan trioleate.

19. A pharmaceutical aerosol according to claim 11, wherein the operating pressure of said pharmaceutical aerosol is 2 to 100 bar.

20. A pharmaceutical aerosol according to claim 19, wherein the operating pressure of said pharmaceutical aerosol is 3 to 50 bar.

21. A pharmaceutical aerosol comprising:

micronized pharmaceutical particles; and a propellant mixture, wherein said propellant mixture exists in a subcritical state and includes at least one component from a first class of propellant gases and at least one component from a second class of propellant gases, said first class comprising propellant gases having an evaporation enthalpy at 25° C. of 200 kJ/kg or less and a vapor pressure at 25° C. of 20 bar or more, and said second class comprising propellant gases having an evaporation enthalpy at 25° C. of 300 kJ/kg or more and a vapor pressure at 25° C. of 10 bar or less, wherein at least about 80 wt. % of said micronized pharmaceutical particles have a diameter of less than 8 µm.

22. The pharmaceutical aerosol of claim 21, wherein at least about 80 wt. % of said micronized pharmaceutical particles have a diameter of less than 5 µm.

23. The pharmaceutical aerosol of claim 21, wherein said propellant mixture is present as a percentage content of 80 to 99.99 wt. % relative to said pharmaceutical aerosol.

24. The pharmaceutical aerosol of claim 21, wherein said pharmaceutical is present in a dissolved or suspended state in said pharmaceutical aerosol as a percentage content of 0.01 to 5 wt. % relative to said pharmaceutical aerosol.

25. The pharmaceutical aerosol of claim 21, wherein said pharmaceutical is chosen from the active ingredients budesonide, salbutamol, beclometason-17,21-dipropionate, terbutaline sulfate, disodium cromoglicinic acid, ipratropium bromide, amphotericin B and combinations thereof.

26. The pharmaceutical aerosol of claim 21, wherein said pharmaceutical aerosol also contains solubilizers for said pharmaceutical.

27. The pharmaceutical aerosol of claim 26, wherein said solubilizers are chosen from alcohols, water and acetone.

28. The pharmaceutical aerosol of claim 21, wherein said pharmaceutical aerosol also contains surfactants.

29. The pharmaceutical aerosol of claim 28, wherein said surfactants are chosen from oleic acid, lecithin and sorbitan trioleate.

30. The pharmaceutical aerosol of claim 21, wherein the operating pressure of said pharmaceutical aerosol is 2 to 100 bar.

31. The pharmaceutical aerosol of claim 30, wherein the operating pressure of said pharmaceutical aerosol is 3 to 50 bar.

* * * * *